United States Patent [19]

Peet et al.

[11] Patent Number: 4,510,327
[45] Date of Patent: Apr. 9, 1985

[54] PROCESS FOR MAKING ALKALI-METAL TETRAORGANYLBORATES

[75] Inventors: William G. Peet, Elkton, Md.; Frederick N. Tebbe, Hockessin, Del.

[73] Assignee: E. I. Du Pont de Nemours and Company, Wilmington, Del.

[21] Appl. No.: 482,597

[22] Filed: Apr. 6, 1983

[51] Int. Cl.³ .............................................. C07F 5/02
[52] U.S. Cl. ..................................................... 568/1
[58] Field of Search ........................ 260/462 R; 568/1

[56] References Cited

U.S. PATENT DOCUMENTS

| 2,853,525 | 9/1958 | Wittig et al. | |
| 3,311,662 | 3/1967 | Washburn et al. | |
| 4,045,495 | 8/1977 | Nazarenko et al. | 568/1 |
| 4,046,815 | 9/1977 | Nazarenko et al. | 568/1 |
| 4,076,756 | 2/1978 | Nazarenko et al. | 568/1 |
| 4,082,811 | 4/1978 | Shook | 568/1 |
| 4,134,923 | 1/1979 | Reimer | 568/1 |
| 4,177,215 | 12/1979 | Seidel | 568/1 |
| 4,251,468 | 2/1981 | Nazarenko et al. | 568/1 |

OTHER PUBLICATIONS

Hough et al., J. Am. Chem. Soc. 80: 1828, (1958).
Schlesinger et al., J. Am. Chem. Soc. 75: 199, (1952).
Grassberger et al., Angew. Chem. Int. Ed. 8: 275, (1969).

Primary Examiner—Helen M. S. Sneed
Attorney, Agent, or Firm—Scott G. Hallquist

[57] ABSTRACT

Alkali-metal tetraorganylborate compounds of formula $MBR_4$ are prepared by reacting triorganylboranes $R_3B$ with alkali-metal hydroxide or alkoxide compounds of the formula $MOR^1$.

18 Claims, No Drawings

PROCESS FOR MAKING ALKALI-METAL TETRAORGANYLBORATES

BACKGROUND OF THE INVENTION

The present invention relates to a process for halide-free synthesis of alkali-metal tetraorganylborate compounds.

Tetraorganylborate compounds have a broad spectrum of utility. Tetraalkylborate compounds are used as alkylating agents, polymerization catalysts, and polymer stabilizers. The most widely-reported tetrarylborate, sodium tetraphenylborate, is an important analytical reagent, as well as an NMR chemical shift reagent, a photographic reagent, and a catalyst in several polymerization reactions. Gmelin, *Handbuch der Anorganischen Chemie,* 33/8, Boron Compounds, (1976) discloses a number of uses for sodium tetraphenylborate, including use as a quantitative precipitant of radioactive cesium from reactor waste effluents.

Wittig et al., U.S. Pat. No. 2,853,525, disclose a process for producing sodium tetraphenylborate by reacting a Grignard reagent with a boron trihalide in accordance with the following two-step reaction:

(1)
$$4C_6H_5MgX + BX_3 \rightleftharpoons (C_6H_5)_3B \cdot C_6H_5MgX + 3MgX_2$$

(2)
$$(C_6H_4)_3B \cdot C_6H_5MgX + Na^\oplus \rightleftharpoons (C_6H_5)_4BNa + Mg^\oplus X$$

X in the foregoing formulas is a halide ion.

Washburn et al., U.S. Pat. No. 3,311,662, describe a method of making sodium tetraarylborate compounds, including sodium tetraphenylborate (NaB(Ph)$_4$), by reacting aryl sodium compounds with triarylborons, e.g., $$ArNa + B(Ar)_3 \rightarrow NaB(Ar)_4,$$

or by reacting aryl sodium compounds with boron trihalides, e.g., $$4ArNa + BCl_3 \rightarrow NaB(Ar)_4 + 3NaCl.$$

Ar in the foregoing formulas can be aryl, alkaryl, haloaryl, aryloxyaryl or alkoxyaryl.

Hough et al., *J. Am. Chem. Soc.* 80: 1828 (1958), disclose the following reaction of gaseous diborane with sodium metal to provide sodium borohydride:

$$2Na + 2B_2H_6 \rightarrow NaBH_4 + NaB_3H_8.$$

Schlesinger et al., *J. Am. Chem. Soc.* 75: 199 (1952), disclose a method of preparing sodium borohydride by reacting sodium methoxide or sodium tetramethoxyborohydride with gaseous diborane, e.g.:

$$3NaOCH_3 + 2B_2H_6 \rightarrow 3NaBH_4 + B(OCH_3)_3.$$

In addition, Schlesinger et al. report that lithium ethoxide (LiOC$_2$H$_5$) reacted with diborane to provide lithium borohydride. However, this reference also reports that potassium methoxide "did not react" with diborane to produce potassium borohydrides.

Grassberger et al., *Angew. Chem. Int. Ed.* 8: 275 (1969), disclose a process for preparing alkali-metal tetraorganylborates by reacting alkali-metal tetraethylborates and triorganylboranes at 130°–180° C., e.g., $$3MB(C_2H_5)_4 + 4BR_3 \rightleftharpoons 3MBR_4 + 4B(C_2H_5)_3.$$

M in the foregoing formula is Na or Li; R is a butyloxy, allyloxy, carbyl, methallyl, phenyl, benzyl or pyrrolyl group.

The availability of certain tetraorganyl compounds has been limited by the lack of a direct, efficient, convenient process for their synthesis. Certain methods representative of the prior art are complex, requiring use of gaseous reactants or extensive purification procedures to make tetraorganylborate compounds of a grade suitable for quantitative analysis.

SUMMARY OF THE INVENTION

According to the present invention, a process is provided for making alkali-metal tetraorganylborates of the formula MBR$_4$, comprising reacting a triorganylborane of the formula R$_3$B with a compound of the formula MOR$^1$. In the foregoing formulas, R is a linear or branched-chain alkyl group of 1 to 6 carbon atoms, an aryl or substituted aryl group of 6 to 12 carbon atoms, or an aralkyl group of 7 to 9 carbon atoms. R$^1$ is hydrogen or an alkyl group having from 1 to 6 carbons, and M is Li, Na, K or Cs.

DETAILED DESCRIPTION OF THE INVENTION

The present invention provides a process for making alkali metal tetraorganylborates of the formula MBR$_4$, comprising reacting a triorganylborane R$_3$B with an alkali metal alkoxide or hydroxide MOR$^1$. As previously stated, R can be a linear or branched-chain alkyl group of from 1 to 6 carbon atoms, an aryl or substituted aryl group of 6 to 12 carbon atoms, or an aralkyl group of 7 to 9 carbons. Aryl substituents can be any group which does not itself take part in the reaction, for example, alkyl, aryl, amine, or alkoxide. Preferably, R is methyl, ethyl, phenyl, napthyl or benzyl. Most preferably, R is phenyl. M can be Li, Na, K or Cs, of which Na is preferred. R$^1$ can be hydrogen or an alkyl group, linear or branched, of up to 6 carbons. For cost and availability considerations, preferably R$^1$ is hydrogen, methyl or isopropyl. For yield considerations, R$^1$ is preferably t-butyl.

The synthesis of tetraorganylborates according to the present invention is believed to proceed by one or more of the following stoichiometries:

(1) $2R_3B + MOR^1 \rightarrow MBR_4 + R_2BOR^1$ (2) $3R_3B + 2MOR^1 \rightarrow 2MBR_4 + RB(OR^1)_2$ (3) $4R_3B + 3MOR^1 \rightarrow 3MBR_4 + B(OR^1)_3.$ Examples of tetraalkylborate compounds which can be made by the process of the invention include alkali metal salts of tetramethylborate, tetraethylborate, tetra(i-propyl)borate, tetra(i-butyl)borate and tetra(n-butyl)borate. A preferred process is one in which triethylborane is reacted with sodium methoxide to produce sodium tetraethylborate, a useful alkylating agent.

Examples of tetraarylborate compounds accessible by the process of the present invention include alkali metal salts of tetraphenylborate, tetratolylborate, tetrafluorophenylborate, tetraethylphenylborate, tetramethoxyphenylborate, tetraphenoxyphenylborate, and tetranaphthylborate. Processes for making sodium tetraphenylborate and sodium tetranaphthylborate are preferred, considering the utility of these compounds as analytical reagents for determination of potassium, cesium and rubidium.

Tetraaralkylborate compounds which can be produced according to the process of the invention include alkali metal salts of tetrabenzylborate and tetraphenethylborate. A process for producing sodium tetrabenzylborate, a useful reducing agent, is preferred. Suitable molar ratios of $R_3B$ to $MOR^1$ reactants range from about 0.3 to about 3.0, but the optimal ratio is dependent upon the values of M, R and $R^1$. In a particular synthesis, optimal ratios can be determined empirically to increase yield. Where R is phenyl, M is Na, and $R^1$ is isopropyl, a ratio about 1.3 to about 1.5 is preferred.

In the method of the invention a solvent can be used but is not required. Inert solvents, particularly hydrocarbon solvents such as toluene, decahydronaphthalene, xylene, benzene or cyclohexane, can increase product yield and are therefore preferred. Cyclohexane is an especially preferred solvent. The process of the invention can be conducted in an autoclave. Alternatively, the process of the invention can be conducted in an open system, in which by-products are distilled from the reaction mixture at reaction temperature.

The process of the invention is typically conducted at temperatures from about 100° C. to about 400° C., preferably from about 180° C. to about 200° C. The process of the invention can be conducted below 100° C. and above 400° C. However, below 100° C., reaction rates are quite slow, and above 400° C., a decomposition side reaction can result.

Due to the possibility of reaction of alkoxide and triorganylborane starting materials with oxygen or water, the process of the present invention is preferably conducted in a dry, inert atmosphere, for example, argon or nitrogen. For cost considerations, nitrogen is preferred.

The most preferred process of the invention is a process for making sodium tetraphenylborate. It has been found that reaction of triphenylborane with sodium isopropoxide in about a 7:5 molar ratio, at a temperature from about 180° C. to about 200° C., produces sodium tetraphenylborate in high yield.

The process of the invention exhibits several advantages in comparison to other processes known in the art. First, the process of the invention is a convenient one-step reaction. Second, this process provides recyclable by-products. Third, the process of the invention is broadly applicable to provide a wide spectrum of tetraalkylborates and tetraarylborates. Fourth, high yields of product are provided using low-cost reagents, and inconvenient gaseous reactants are generally not required. Fifth, this synthesis does not employ halide-containing reactants, which is a significant consideration in preparing pure tetraorganylborate for use in quantitative analysis of cesium or potassium.

The following examples are provided to further illustrate the process of the invention. In the examples, all reactions were conducted under an atmosphere of inert nitrogen. All temperatures are reported in degrees Celsius. In Examples 1–6, the desired product, sodium tetraphenylborate, was converted to its cesium salt as a convenience for analysis.

EXAMPLES

Example 1

Preparation of $NaB(Ph)_4$ by Reaction of $NaOCH_3$ and $B(Ph)_3$

A reaction mixture was formed by mixing triphenylboron ($B(Ph)_3$) (1.0 g, 4.1 mmol) and sodium methoxide ($NaOCH_3$) (0.1 g, 1.8 mmol), and heating the resulting mixture, with stirring, above the melting point of $BPh_3$ (>200°). After about 15 minutes, the resulting slurry was cooled to about 23°, and toluene added to extract by-products. Undissolved product, $NaBPh_4$, was separated from the toluene extract by filtration, dissolved in water, and contacted with a molar excess of cesium fluoride (CsF) in aqueous solution. The resulting white precipitate was filtered, washed with water and ethyl ether, and dried under vacuum. The final product (0.05 g, 0.11 mmol) was analyzed by infrared spectroscopy. The spectrum obtained was identical to that observed in an analysis of a sample of cesium tetraphenylboron ($CsBPh_4$) prepared by reacting CsF and $NaBPh_4$ obtained from commercial sources.

Example 2

Preparation of $NaBPh_4$ by Reaction of $NaOCH_3$ and $BPh_3$ in Decahydronaphthalene A reaction mixture was formed by adding 0.21 g (3.9 mmol) $NaOCH_3$ to 3 ml decahydronaphthalene. The mixture was boiled, reducing the total volume to about 1 ml by azeotropic removal of $CH_3OH$ and $H_2O$. The resulting slurry was cooled to about 23° and 1.0 g (4.1 mmol) $BPh_3$ added. This mixture was heated to about 200°, and held at this temperature for about 7 minutes, with stirring. The mixture was cooled, 20 ml toluene added, and the resulting mixture filtered. The toluene-insoluble solids which collected on the filter were washed with an additional aliquot of toluene before redissolving in water. The resulting aqueous solution of $NaBPh_4$ was reacted with a molar excess of CsF, providing a precipitate which was filtered, washed with water and ether, and dried under vacuum. The resulting product ($CsBPh_4$, 0.73 g, 1.6 mmol) was characterized by HPLC (high performance liquid chromatography), X-ray analysis, and infrared spectroscopy. In addition, the crystal morphologies of the product and a sample of authentic $CsBPh_4$ were compared using a scanning electron microscope. The results of these analyses confirmed that $CsBPh_4$ had been prepared.

Analysis Calcd. for $C_{24}H_{20}BCs$: C, 63.76; H, 4.46; B, 2.39; Cs, 29.39. Found: C, 63.70; H, 4.61; B, 2.39; Cs, 29.44.

Example 3

Preparation of $NaBPh_4$ by Reaction of $NaO(i-Pr)$ with $BPh_3$ 5.0 g (21 mmol) triphenylboron were dissolved in 25 ml hot toluene and added to a slurry of sodium isopropoxide ($NaO(i-Pr)$) (1.27 g, 15 mmol) in hot toluene. A yellow precipitate formed as the resulting mixture was heated to boiling. The toluene was then removed by distillation. At approximately 190°, the mixture solidified and high boiling liquids began to distill. After heating the remaining solids for about 30 minutes at about 190°, the solids were cooled and washed with toluene. Dissolving the resulting product ($NaBPh_4$) in water, followed by treatment with a solution of cesium fluoride, provided a white precipitate, which was dried under vacuum to give 4.74 g, (10.5 mmol). Characterization by $^1$H NMR, IR and HPLC indicated that the product was sodium tetraphenylboron.

Analysis Calcd. for $C_{24}H_{20}BCs$: C, 63.76; H, 4.46 Found: C, 63.91; H, 4.44.

Example 4

Preparation of NaBPh$_4$ by Reaction of NaOH and BPh$_3$

A reaction mixture was formed by adding 0.12 g (3 mmol) NaOH powder and 1.0 g (4.1 mmol) BPh$_3$ to 2 ml decahydronaphthalene. This mixture was heated to its approximate boiling point and held at this temperature for about 20 min. Distillation of some volatile components was observed. A white solid formed which was collected on a filter, washed with toluene, dissolved in water, and reacted with a molar excess of CsF. HPLC and infrared spectroscopic analysis indicated that the resulting product (0.42 g, 0.9 mmol) was CsBPh$_4$.

Examples 5 and 6

Preparation of NaBPh$_4$ and NaB(CH$_2$Ph)$_4$

Examples 5 and 6 were conducted by a procedure substantially similar to that reported for Example 4, using the reagents indicated in Table 1, below. Infrared spectroscopy, proton-NMR spectra, and C, H, B and Cs analyses of cesium salts prepared from the resulting sodium tetraorganylborates confirmed the presence of the products indicated.

TABLE 1

| Example | R$_3$B | MOR$^1$ | MBR$_4$ |
| --- | --- | --- | --- |
| 5 | Ph$_3$B (4.1 mmol) | NaO(t-Bu) (3.1 mmol) | NaBPh$_4$ (2.4 mmol) |
| 6 | (PhCH$_2$)$_3$B (3.5 mmol) | NaO(i-Pr) (2.7 mmol) | NaB(CH$_2$Ph)$_4$ (1.2 mmol) |

Example 7

Autoclave Procedure for Preparation of NaBPh$_4$ from BPh$_3$ and NaO(i-Pr) in Cyclohexane A reaction mixture was formed by adding 0.36 g (16 mmol) sodium metal to 20 ml cyclohexane. 1.15 ml (15 mmol) isopropanol, which had previously been dried using 4A molecular sieves, was added, and the resulting mixture heated to about 70°–80° for one hour. The resulting slurry of NaO(i-Pr) was transferred to an autoclave. 5.0 g (21 mmol) triphenylboron and about 20 ml additional cyclohexane were added to the slurry. The autoclave was slowly heated to about 190°–195° and held at this temperature for about two hours. After cooling overnight, the autoclave contents were filtered through a medium-porosity glass frit. The filtered solid material was carefully washed with three 25 ml aliquots of toluene followed by 25 ml cyclohexane. The resulting white solid was dried in a stream of nitrogen gas. The final yield of sodium tetraphenylborate was 4.60 g (13.5 mmol).

We claim:

1. A process for making alkali-metal tetraorganyl borates of the formula MBR$_4$, comprising reacting a triorganylborane of the formula R$_3$B with a compound of the formula MOR$^1$ at a temperature sufficient to result in formation of a compound of the formula MBR$_4$, wherein R is an alkyl group of 1 to 6 carbons, an aryl or substituted aryl group of 6 to 12 carbons, or an aralkyl group of 7 to 9 carbons;

R$^1$ is hydrogen or an alkyl group having from 1 to 6 carbons; and

M is Li, Na, K or Cs.

2. A process according to claim 1 conducted at a temperature from about 100° C. to about 400° C.

3. A process according to claim 2 wherein the temperature is from about 180° C. to about 200° C.

4. A process according to claim 3, wherein the triorganylborane and the compound of the formula MOR$^1$ are reacted in the presence of an inert solvent in an inert atmosphere.

5. A process according to claim 4 wherein M is Na.

6. A process according to claim 5 wherein R is alkyl.

7. A process according to claim 6 wherein R is methyl.

8. A process according to claim 6 wherein R is ethyl.

9. A process according to claim 5 wherein R is benzyl.

10. A process according to claim 5 wherein R is an aryl group.

11. A process according to claim 10 wherein R is naphthyl.

12. A process according to claim 10 wherein R is phenyl.

13. A process according to claim 12 wherein R$^1$ is hydrogen, methyl, isopropyl or t-butyl.

14. A process according to claim 13 wherein R$^1$ is hydrogen.

15. A process according to claim 13 wherein R$^1$ is methyl.

16. A process according to claim 13 wherein R$^1$ is isopropyl.

17. A process according to claim 13 wherein R$^1$ is t-butyl.

18. A process according to claim 13 wherein the inert solvent is selected from the group consisting of cyclohexane, toluene, decahydronaphthalene and xylenes.

* * * * *